United States Patent [19]

Smith

[11] Patent Number: 5,244,456
[45] Date of Patent: Sep. 14, 1993

[54] PODIATRIC BIOBALANCING SYSTEM AND DEVICE

[76] Inventor: Gary H. Smith, 59 Woodthrush Trail West, Medford, N.J. 08055

[21] Appl. No.: 871,344

[22] Filed: Apr. 21, 1992

[51] Int. Cl.⁵ ............................................... A61F 5/00
[52] U.S. Cl. ...................................... 602/39; 128/845
[58] Field of Search ....................... 602/23, 27, 28, 29, 602/39; 128/845, 846, 869, 882

[56] References Cited

U.S. PATENT DOCUMENTS

| | | | |
|---|---|---|---|
| 3,908,643 | 9/1975 | Bliss | 602/39 |
| 4,261,348 | 4/1981 | Haragadon | 602/39 |
| 4,466,425 | 8/1984 | Maggi | 128/845 |
| 4,640,275 | 2/1987 | Buzzese et al. | 128/845 X |
| 4,817,610 | 4/1989 | Lee | 128/845 X |
| 4,941,963 | 7/1990 | Roeder | 602/39 |

Primary Examiner—Robert A. Hafer
Assistant Examiner—Sam Rimell
Attorney, Agent, or Firm—McGlew and Tuttle

[57] ABSTRACT

A method and apparatus for making a cast or measurement of a patient's foot while the leg of the patient is held substantially vertical. A center line is drawn on the back of the patient's leg along a longitudinal axis of the leg. The leg is then placed in a box with a transparent side and this transparent side has a substantially vertical line. The center line on the leg is aligned with the substantially vertical line on the box and then measurements or a cast of the foot is taken.

20 Claims, 7 Drawing Sheets

PODIATRIC BIOBALANCING SYSTEM AND DEVICE

FIELD OF THE INVENTION

The invention relates generally to a system for making casts of a patient's foot, and more specifically to a device, method, and system for making a cast or measurements of a patient's foot while the leg is held in a vertical position. The invention includes a means for locating a central axis of the foot and leg and the central axis is aligned with a vertical positioning line on the device.

BACKGROUND OF THE INVENTION

It has come to applicant's attention that a closely related field to the present invention involves various devices for securely holding a limb and other devices for forming casts of the limb. Patents in this field include Pat. Nos. 1,335,475, 2,185,322, 4,342,451 and 5,042,508. None of these references use a center line on the leg which is to be aligned with a line on a vertical positioning line on the device. Also, none of these references have a method for recording the position of the foot when the leg is substantially aligned vertically.

SUMMARY AND OBJECTS OF THE INVENTION

The invention provides a transparent positioning box used for holding a patient's leg in a vertical position and having a bottom cut out portion for receiving a casting material into which the foot is submerged. Preferably the box includes two adjustable chamber panels made of a transparent material such as plexiglass. The adjustable chamber panels are inserted longitudinally into the casting box and held in place by pegs which are positionable in a plurality of holes on the inside of the transverse surfaces of the box.

A central axis of the patient's leg below the knee is determined by an adjustable caliper having a levelling means to ensure that the calipers are held level, and a marking means such as a pen or pencil. The doctor, or technician runs the calipers vertically from the posterior side of the patient's leg with the caliper tips resting on opposite sides of the patient's leg. The writing means is secured facing the patient's leg between the caliper tongs at the central axis of the tongs. As the calipers are passed down along the leg, a bisecting line or central axis line is marked on the posterior side of the patient's leg. The central axis of the leg can also be determined while the patient is lying on an examining table.

The doctor or technician draws a vertical line on the back surface of the transparent box if one is not already provided. The patient steps one foot into the box and the doctor or technician lines up the central axis of the patient's foot with the vertical line on the box.

Any variances of the line from true vertical can be adjusted by manually moving the leg or be using a balancing means to adjust the bottom surfaces of the foot's posterior end and anterior end.

The balancing means includes a balancing platform having a first set of three plates. Of these first set of plates, a middle plate is hingably connected to a right plate at a first end and the left plate is hingably connected at a second end. A second set of plates consists of a similar triple plate arrangement and is separated from the first set by an adjusting means, such as a threaded rod for adjusting the balancing platform to the size of the patient's foot. A patient's foot normally has a natural tilt of the bottom surface at the posterior end. To compensate for this tilt, the right plate is flipped over the middle plate at the hinge and the angle between the two plates is adjusted by adjusting screws on the middle plate. The adjusting srews are positioned on the plates opposite from the hinge upon which the plate rests. Similarly when the posterior side of the foot tilts downwardly toward the left the left balancing plate is used. The level of the anterior bottom of the foot is adjusted similarly.

When the central axis line on the patient's foot is aligned with the vertical line on the box, the adjustable panel walls are put into position and secured against the opposite sides of the patient's foot. Thereby causing the position of the patient's foot to be held in a manner to ensure that the patients leg is in a substantially vertical position. The foot is then removed the from the box, the balancing platform is removed from the bottom of the box, and a casting material is placed in the bottom of the box. The patient's foot is put back into the box between the adjustable chamber panels, thereby reestablishing the vertical position. The foot is then pressed, or submerged, into the casting material.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

DETAILED DESCRIPTION OF THE PREFERRED EMBODIMENT

Figure 1:
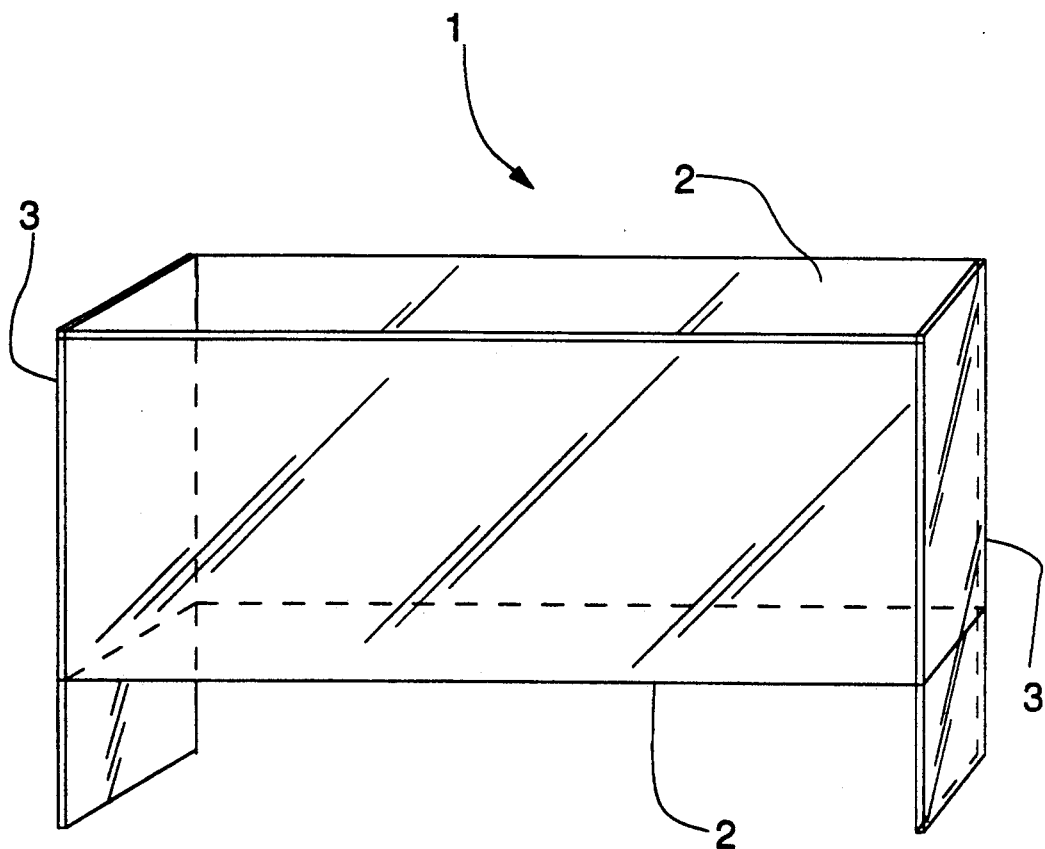
FIG. 1 is a perspective view of a transparent box according to the invention.
Figure 2:
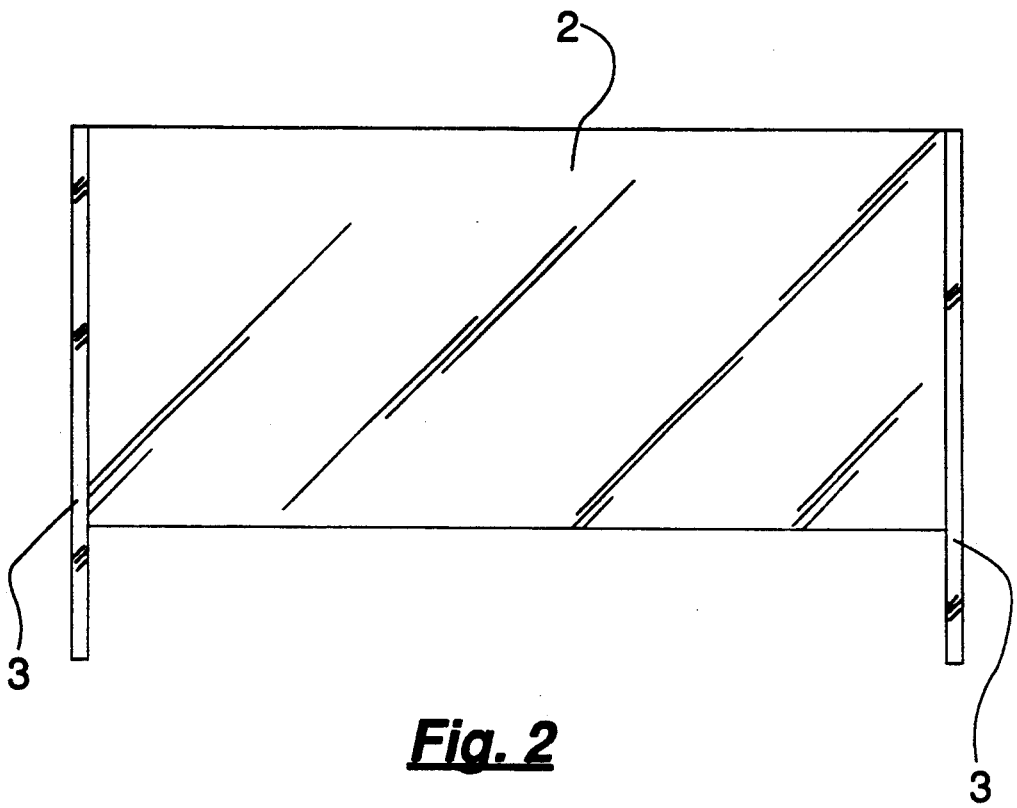
FIG. 2 is a side view of the box according to FIG. 1.
Figure 3:
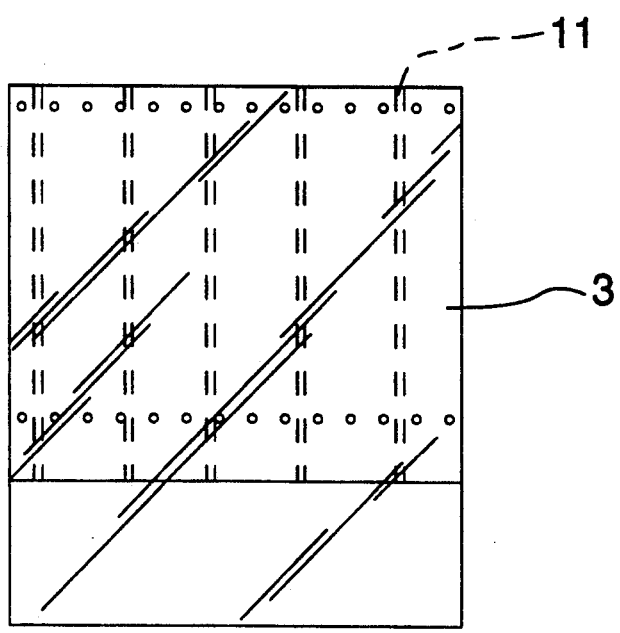
FIG. 3 is an elevational view of one of the transverse sides of the box.
Figure 4:
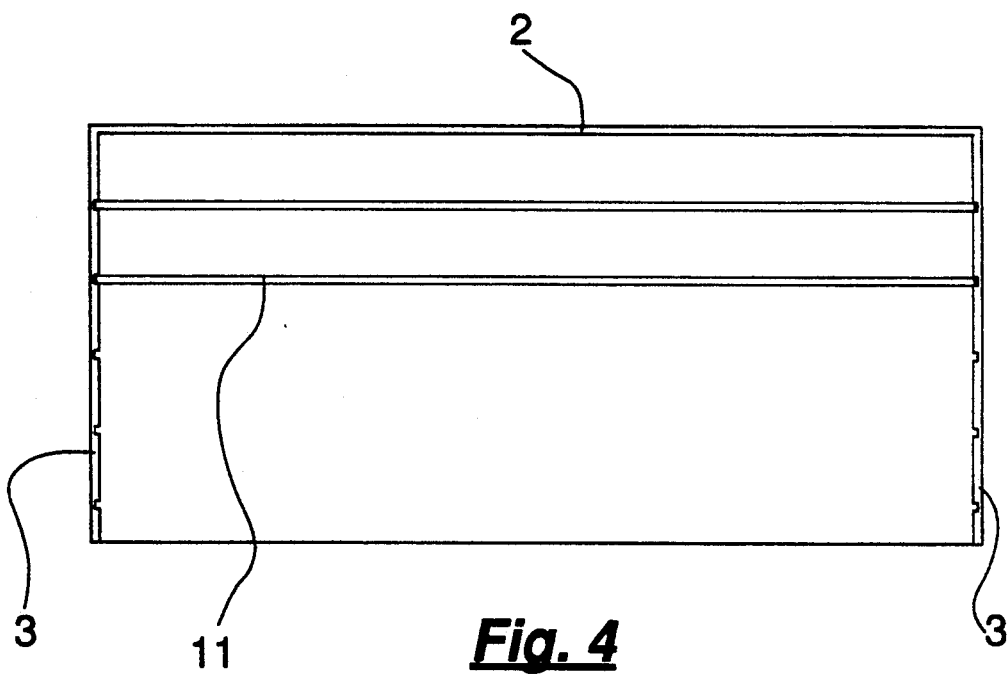
FIG. 4 is a top view of the transparent box showing two chamber panels positioned therein.

Referring to the drawings, and in particular to FIG. 1, the transparent box 1 has two longitudinal sides 2. Two transverse walls 3 are connected to the longitudinal 2 in order to form the transparent box 1. The longitudinal walls 2 are mounted above the ground in order to place objects such as the balancing means or the casting material into the box. At least one of the transverse sides is transparent in order to allow a view from outside the box into the inside of the box. This transparent transverse side has a substantially vertical line placed upon it.

Figure 5:
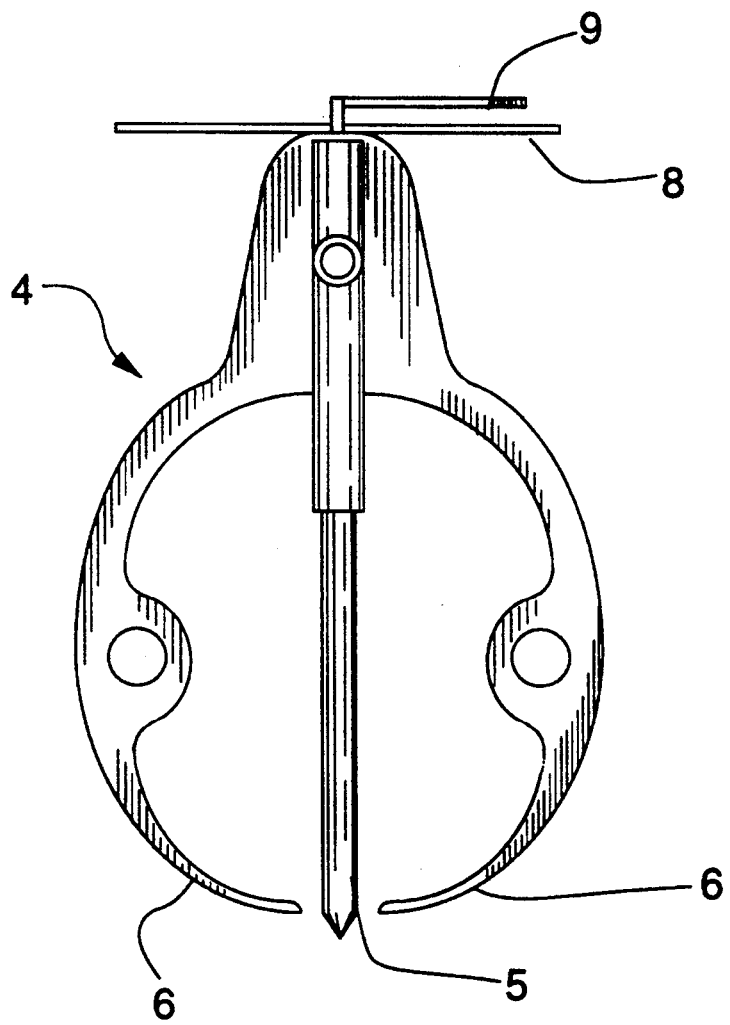
FIG. 5 is a top view of the adjustable caliper.
Figure 6:
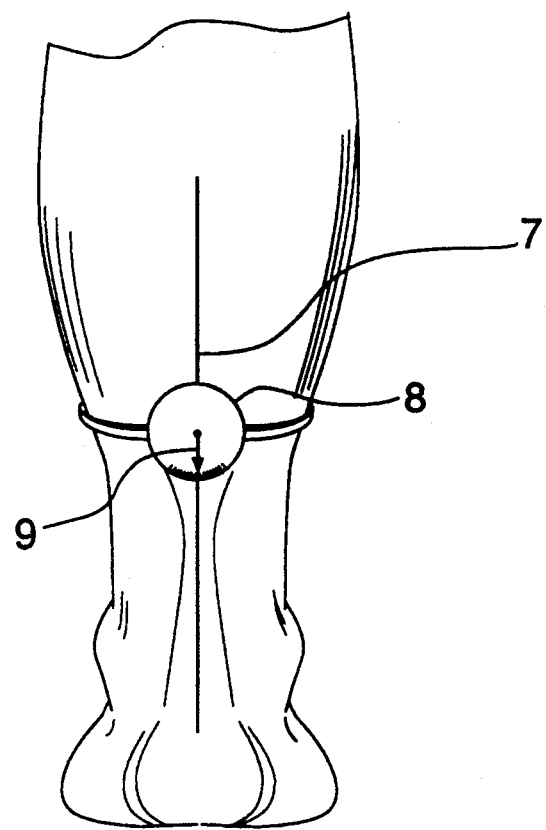
FIG. 6 and FIG. 7 show the adjustable caliper.
Figure 7:
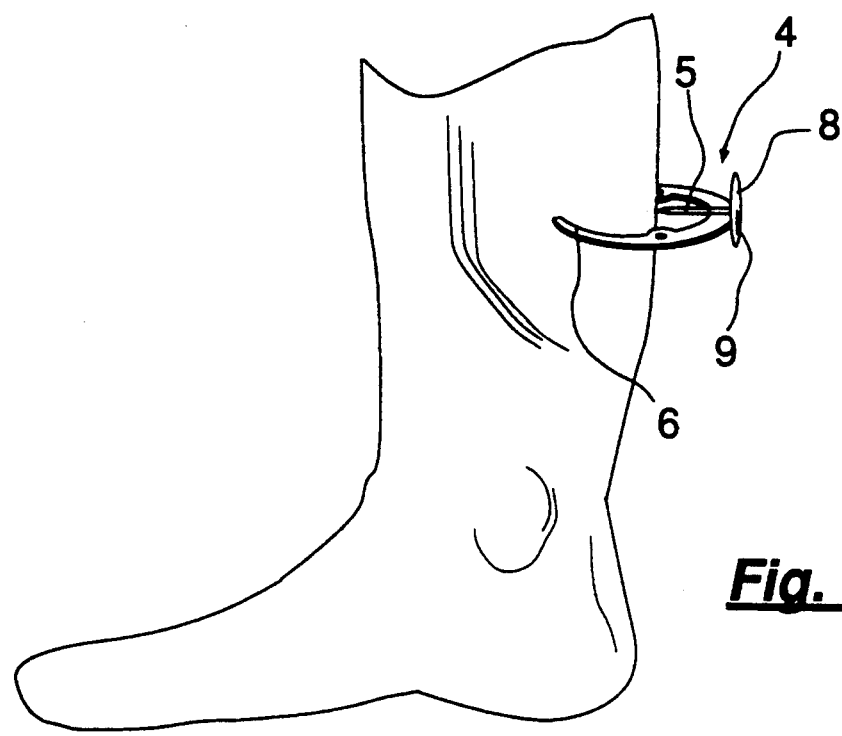
Figure 8:
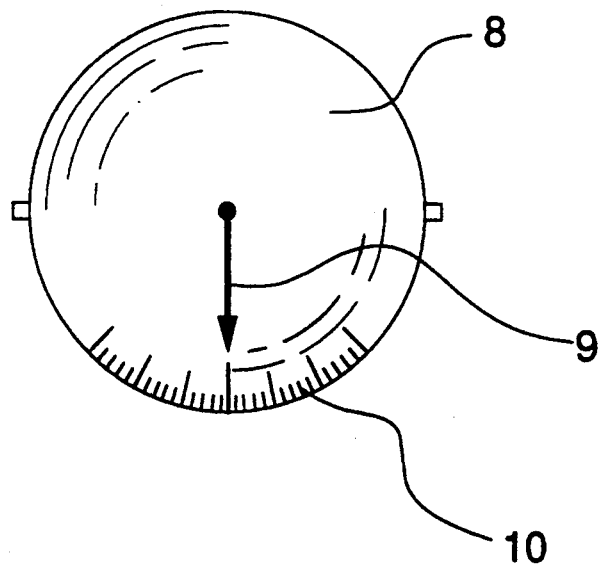
FIG. 8 is a rear view of the caliper levelling means as shown in FIGS. 6 and 7.
Figure 9:
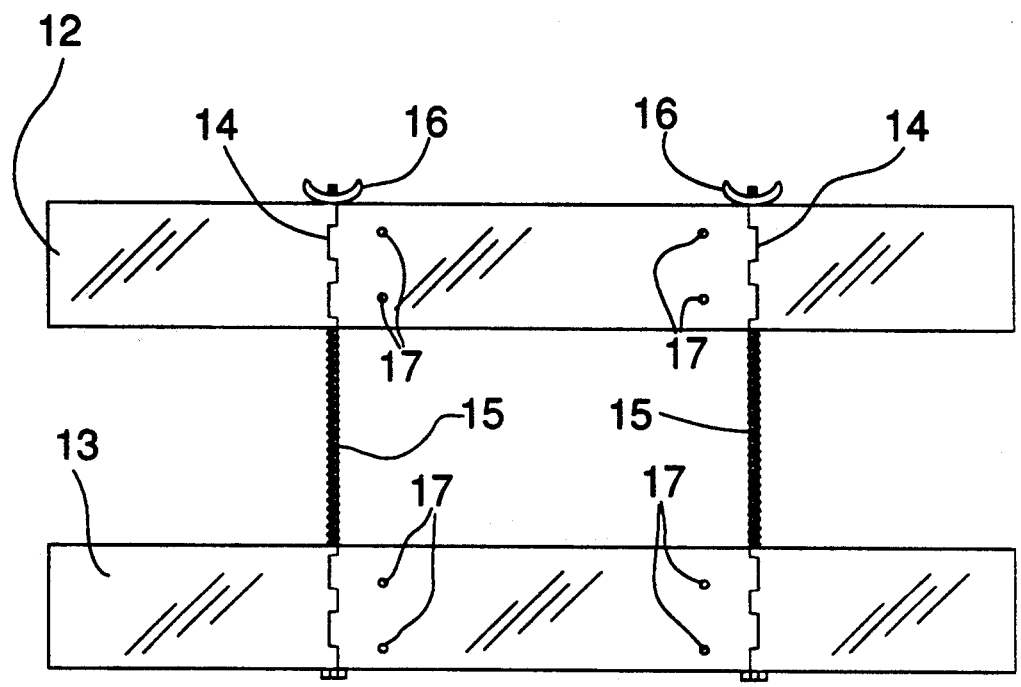
FIG. 9 is a top view of a balancing platform according to the invention.
Figure 10:
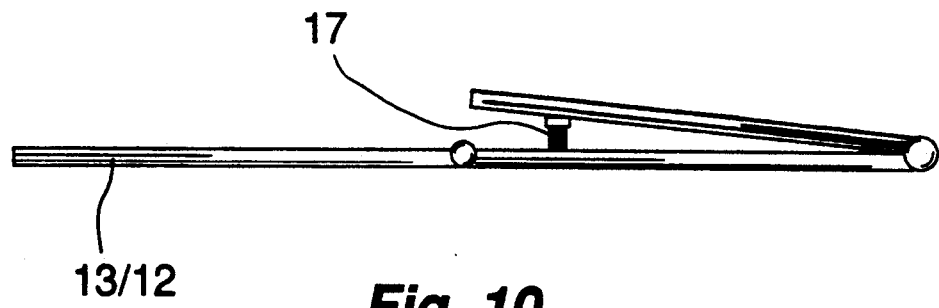
FIG. 10 is a front view of the balancing platform according to FIG. 9.

FIGS. 5, 6 and 7 show an adjustable caliper 4. The adjustable caliper 4 has a marking means 5 connected to it. The adjustable calipers 4 and the marking means 5 are connected in such a way that the adjustable calipers 4 can be used to place a center line along the patient's leg. The adjustable calipers 4 have caliper tongs 6 which are guided along opposite sides of the patient's leg. The marking means 5, which is held equidistant between the caliper tongs, then marks the center line on the patient's leg. A caliper levelling means 8 can be used to hold the adjustable calipers 4 in a level position when the leg to be marked is in a vertical position. The caliper levelling means has an indicator arrow 9 which is downwardly biased by gravity. An indicator scale 10 cooperates with the indicator arrow 9 in order to indicate if the adjustable calipers are being held level as they are passed along the patient's leg as shown in FIGS. 7 and 8.

Once the patient's leg has the center line 7 placed upon it, the leg is then placed into the transparent box 1. The substantially vertical line on the transparent transverse side 3 is compared to the center line on the patient's leg. If the center line of the patient's leg and the substantially vertical line on the transverse side are not substantially aligned, then the leg can either be moved manually or a balancing means is placed under the patient's foot. This balancing means adjusts the level of the bottom surface of the foot. The balancing means is adjusted until the center line 7 and the vertical line 10 on the transparent transverse end 3 are substantially aligned.

Now the chamber panels 11 are fitted into the box and pressed against the leg. The leg and the balancing means are then removed from the transparent box. Casting material is then placed at the bottom of the transparent box in a position where the foot was originally placed. The patient's leg is then put back in the transparent box 1 between the chamber panels 11. The chamber panels 11 hold the leg in the same position that the leg was in while the foot was standing on the balancing means. As the leg is placed in between the chamber panels, the foot is placed into the casting material in order to make an imprint of the foot when the leg is in a substantially vertical position. The chamber panels 11 are slightly shorter in length than the longitudinal sides 2 and the chamber panels 11 can be attached to the transverse sides 3 by means of pegs placed in peg holes on the transverse ends.

The balancing means can consist of a first set of three plates 12 and a second set of three plates 13. Each of these sets of plates has a middle plate and two end plate. One end plate being pivotally connected to one edge of the middle plate, and the other end plate being pivotally connected to another edge of the middle plate. Depending on which way the foot is to be tilted, one of the end plates is folded on top of the middle plate, and the other end plate is left open. Adjustment screws 17 screw into the middle plate and hold the folded end plate at an adjustable angular distance from the middle plate.

Once the leg has been aligned by the balancing means, the balancing means can be removed and the angular distance between the plates can be measured. This measured angular distance can then be used to determine the degree of corrective measures needed to be applied to the foot to have the leg vertical.

The first and second set of plates 12 and 13 are preferably connected to each other by threaded rods 14 passing through the pivots. The distance between the first and second set of plates 12/13 is also preferably made adjustable by the use of a spring 15 forcing the plates 12/13 apart and a wingnut 16 on the threaded rod 14 for limiting the distance the plates 12/13 can be spaced together. The anterior, or front of the foot, is placed on one set of plates, and the posterior or rear side of the foot, is placed on the other set of plates. The adjustment screws 17 are then turned in order to adjust the level of the foot, to cause the center line 7 of the leg to substantially align with the substantially vertical line 11 on the transparent transverse side.

The transparent transverse side can have a plurality of substantially vertical lines 11, and the center line 7 on the leg is then aligned with the nearest substantially vertical line 11. All the sides of the transparent box 1 can also be made transparent in order to allow easier viewing and positioning of the leg. The chamber panels can also be made transparent. The chamber panels are necessarily made shorter in length then the longitudinal sides.

This device and method allows easy, quick and accurate imprints of the foot while the leg is held substantially vertical. This is very useful in determining leg disorders and in fitting corrective footwear to correct such disorders.

While a specific embodiment of the invention has been shown and described in detail to illustrate the application of the principles of the invention, it will be understood that the invention may be embodied otherwise without departing from such principles.

What is claimed is:

1. A podiatric biobalancing method comprising the steps of:
    providing a transparent box having a transparent side, said transparent side having a substantially vertical line;
    marking a center line on a leg of a patient;
    placing the leg of the patient inside said transparent box;
    moving the leg inside said transparent box to cause said center line of the patient's leg to be aligned with said substantially vertical line on said transparent box;
    placing chamber panels in said transparent box, said chamber panels being placed against the leg for securely holding the leg aligned with said center line of said transparent box;
    raising the securely held leg;
    placing recording means under a foot of the leg;
    recording a position of the foot of the securely held leg in order to make a recording of the foot position for podiatric biobalancing.

2. A method in accordance with claim 1 wherein:
    said recording is performed by placing a casting material under the foot of the leg; and
    lowering the securely held leg to place the foot in said casting material in order to make a lasting imprint of said position of the foot.

3. A method in accordance with claim 1, wherein:
    said recording is performed by a balancing means being placed under the foot of the leg and said balancing means recording an amount of movement of the foot which is needed for said aligning of said center line with said substantially vertical line of said transparent box.

4. A method in accorandance with claim 1, further comprising:
    providing an adjustable calipers with caliper tips, said adjustable calipers holding a marking device substantially equidistant from said caliper tips;

passing said caliper tips in a substantially straight line along substantially opposite sides of the leg; and pressing said marking device along said leg during said passing of said caliper tips along the leg in order for said marking of said center line.

5. A method in accordance with claim 4, further comprising:

providing a levelling means on said adjustable calipers for holding said adjustable calipers level.

6. A method in accordance with claim 1, wherein:

said holding of said leg by said chamber panels is done by inserting pegs into bores defined by said transparent box.

7. A podiatric biobalancing system comprising:

a transparent box having a transparent side, said transparent side having a substantially vertical line;

adjustable caliper means for marking a center line on a leg of a patient;

chamber panel means for holding said center line of the leg of the patient aligned with said substantially vertical line on said transparent side of said transparent box; and recording means for recording a postion of a foot when said center line of the leg is aligned with said substantially vertical line.

8. A system is accordance with claim 7, wherein:

said recording means is casting material for receiving and leaving a lasting imprint of the foot.

9. A system in accordance with claim 7, wherein:

said recording means is a balancing means for providing an angled surface to a bottom surface of the foot, said angled surface remaining stationary after the foot is removed, and an angle of the stationary angled surface being measurable.

10. A system in accordance with claim 9, wherein:

said angled surface contacts a first portion of said bottom surface of the foot; and said balancing means provides another angled surface contacting a second portion of said bottom surface of the foot.

11. A system in accordance with claim 10, wherein:

said balancing means has a first set of three plates and a second set of three plates; in each set of three plates two end plates are pivotally connected to a middle plate on substantially opposite edges of said middle plate respectively, one of said end plates is folded over on said middle plate to provide a surface angled in a first direction, and an end plate opposite of said one end plate is folded over to provide a surface angled in a second direction, elevation screws between said end plates and said middle plate adjust an angle of said angled surfaces.

12. A device in accordance with claim 10, wherein:

said angled surface and said another angled surface are spaced apart by a distance.

13. A system in accordance with claim 12, wherein: said distance is adjustable.

14. A system in accordance with claim 13, wherein:

said distance is adjustable by a threaded rod passing through said angled surface and said another angled surface.

15. A system in accordance with claim 14, further comprising:

a spring substantially concentric with said threaded rod biasing said angled surface and said another angled surface apart; and;

a threaded nut on said threaded rod limits how far apart said angled surface and said another angled surface are spaced.

16. A system in accordance with claim 7, wherein:

said adjustable caliper means has caliper tips and a marking tip for marking said center line substantially equidistant from said caliper tips.

17. A system in accordance with claim 7, further comprising:

level means on said adjustable calipers for holding said adjustable calipers level.

18. A system in accordance with claim 17, wherein:

said system level means has a gravity-based indicator and a scale for indicating an angle of said adjustable calipers.

19. A system in accordance with claim 7, wherein:

said chamber panel means has chamber panels connected to transverse sides of said transparent box.

20. A system in accordance with claim 7, wherein:

said transparent box is open at a bottom portion at one side for inserting and removing said recording means.

* * * * *